United States Patent
Kulkarni et al.

(10) Patent No.: US 6,524,446 B2
(45) Date of Patent: Feb. 25, 2003

(54) PROCESS FOR SYNTHESIS OF A PORPHYRIN COMPOUND USING A MOLECULAR SIEVE CATALYST UNDER MICROWAVE IRRADIATION

(75) Inventors: Shivanand Janardan Kulkarni, Andhra Pradesh (IN); Kondapuram Vijaya Raghavan, Andhra Pradesh (IN); Radha Kishan Motkuri, Andhra Pradesh (IN); Srinivas Nagabandi, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/818,280

(22) Filed: Mar. 27, 2001

(65) Prior Publication Data

US 2002/0143175 A1 Oct. 3, 2002

(51) Int. Cl.$^7$ ............................................. C07D 487/22
(52) U.S. Cl. .................................. 204/157.72; 540/145
(58) Field of Search ...................... 540/145; 204/157.72

(56) References Cited

PUBLICATIONS

Hu Ximing, Huanan Ligong Daxue Xuebao, Ziran Kexueban (1999), 27(10), 11–15 "Study on the microwave–induced sythesis of tetraphenylporphyrin".*

Algarra, Felipe, et al. "Condensation of Pyrrole with Aldehydes in the Pressence of Y Zeolites and Mesoporous MCM–41 Aluminosilicate: on the Ecapsulation of Porphyrin Precursors" Chemical Abstract Service, Database No. 129:67626 (XP002184581) (19998), 22(4), PP 33–338.

Petit, A. et al: "Microwave Irradiation in Synthesis of Tetrapyrrolic Compounds" Chemical Abstract Service, Database No. 116214210 (XP002184582 (1992) 22(8) PP 1132–42.

* cited by examiner

*Primary Examiner*—Mark L Berch
*Assistant Examiner*—Kahsay Habte
(74) *Attorney, Agent, or Firm*—Ladas & Parry

(57) ABSTRACT

The present invention provides an improved process for synthesis of porphyrin compounds of the general formula 1

Formula 1

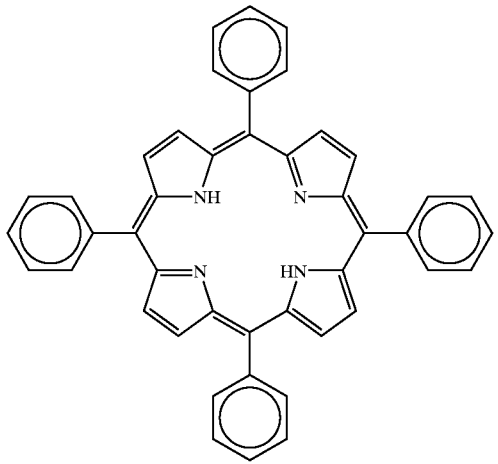

from pyrrole and aromatic aldehyde over zeolite molecular sieve catalysts using microwave heating, (solvent free) to provide an eco-friendly, economical, faster and selective heterogeneous method.

10 Claims, No Drawings

PROCESS FOR SYNTHESIS OF A PORPHYRIN COMPOUND USING A MOLECULAR SIEVE CATALYST UNDER MICROWAVE IRRADIATION

FIELD OF INVENTION

The present invention relates to a process for synthesis of a porphyrin compound using a molecular sieve catalyst under microwave radiation. More particularly, the present invention relates to a process for synthesis of tetraaryl porphyrin by reacting pyrrole and aromatic aldehyde under microwave irradiation, which is a solvent free system using a specific zeolite catalyst. The invention also relates to a process for the synthesis of tetraphenyl porphyrin by reacting pyrrole with benzaldehyde in presence of zeolite molecular sieves under microwave irradiation. The present invention relates to synthesis of porphyrin compounds over solid acid catalyst.

This invention provides a non-corrosive, eco-friendly process, where the catalyst can be recyclable and reuse for many times, no work up procedure, no-wastage of the compounds (i.e. high atom selectivity), simple sample extraction and high selectivity of products.

BACKGROUND OF THE INVENTION

Porphyrin compounds as well as methods for synthesising the same are well recognised in the art. However, porphyrin compounds and other pyrrole compounds are expensive. For example porphyrine is offered at costs as high as $15,000/g. Even though many catalysts such as organic and inorganic acid catalysts are known for the synthesis of porphyrins, the catalysts have at best limited facility for reuse and the yields are very low. Another disadvantage of the prior art processes for the synthesis of porphyrins using such catalysts is that impure corroles are formed making it difficult to separate the pure compound.

The first such report of synthesis of porphyrin molecules under microwave irradiation by A. Petit et al (Synthetic Communication 22 (8) (1992) 1139) employed silica alumina, clay and montmorillonite as a catalyst. However, the results were very poor and not more than 10%.

It is therefore important to develop a process for the synthesis of porphyrins with good yield and where catalyst is reusable thereby resulting in economy of costs.

Zeolite catalysts are known in the art for several processes. Zeolites of ZSM series are available from Conteka, Swedan. Methods for producing them are described in detail in U.S. Pat. No. 3,702,886 (ZSM-5). C. T. Kresge, M. E. Leonowicz, W. J. Roth, J. C. Vartuli and J. S. Beck, Nature 359 (1992) describe the synthesis of MCM-41 by an aqueous solution of aluminum isopropoxide. An aqueous solution of sodium hydroxide (0.3 g) was added to aluminum isopropoxide (0.38 g) in 50 ml beaker and stirred in hot conditions, till a clear solution was formed. Then 9.4 ml of tetraethyl ammonium hydroxide (TEAOH) and Ludox colloidal silica (9.26 g) were added drop wise while stirring at room temperature. Then hexadecyl tri-methylammonium bromide (10.55 g) was added slowly to the above solution. The pH of the mixture was maintained at 11.0–11.5. Finally, the gel mixture was transferred into an autoclave and heated at 100° C. for 24 h. The solid product was recovered by filtration, washed with deionized water and dried in air. All the as-synthesized samples were calcined at 773 K in air.

OBJECTS OF THE INVENTION

The main object of the present invention is to provide a selective, solvent free, eco-friendly, economical process for synthesis of tetraaryl porphyrines.

This and other objects of the invention have been achieved by using a zeolite molecular sieve as the catalyst for the microwave radiation method for the synthesis of porphyrins.

SUMMARY OF THE INVENTION

Accordingly the present invention provides a process for the synthesis of a tetraaryl porphyrin of the formula 1

Formula 1

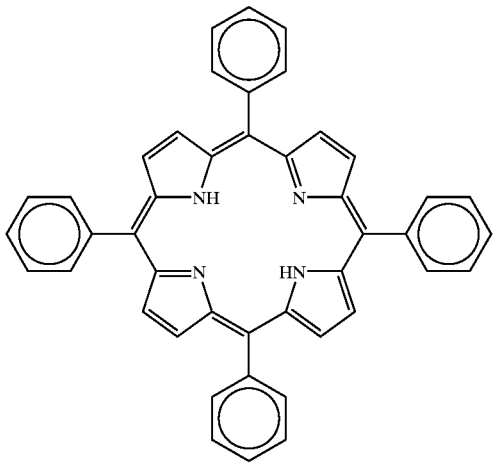

said process comprising reacting the corresponding pyrrole and aldehyde in a solvent free system under microwave radiation in the presence of a zeolite molecular sieve catalyst to obtain the compound of formula 1.

In one embodiment of the invention, the zeolite molecular sieve catalyst used is in alkali ion form, ammonium ion form or proton form.

In a further embodiment of the invention, the alkali ion is selected from sodium and postassium.

In another embodiment of the invention, the zeolite molecular sieve catalyst is selected from the group consisting of MCM-41, Al-MCM-41, HY, SAPO-5, ZSM 5 and HZSM-5 (30).

In another embodiment of the invention, the aromatic aldehyde is of the general formula RPhCHO wherein R in the ortho, meta and para positions is selected from the group consisting of methoxy, N, N, dimethyl, hydroxy and nitro.

In a further embodiment of the invention, the aromatic aldehyde used is selected from the group consisting of benzaldehyde, o/m/p-methoxy benzaldehyde, o/m/p-methyl benzaldehyde, o/m/p-nitro benzaldehyde, m/p-hydroxy benzaldehyde, N,N, dimethyl benzaldehyde, 3,4,5 tri methoxy benzaldehyde.

In a further embodiment of the invention, the pyrrole to aldehyde molar ratio is in the range of 1:1 to 1:4.

In yet another embodiment of the invention, the catalyst is regenerated by burning out the carbon deposited thereon by passing air through the catalyst layer at a temperature in the range of 450° C. to 550° C.

In another embodiment of the invention, the yield of the compound of formula 1 is 23.5%.

DETAILED DESCRIPTION OF THE INVENTION

Tetraphenyl porphyrines by reacting pyrroles with aromatic aldehyde under microwave irradiation in presence of a catalyst, wherein the catalyst is a commercially available or as synthesized catalyst.

The aromatic aldehydes used in the present invention includes benzaldehyde, o/m/p-methoxy benzaldehyde, o/m/p-methyl benzaldehyde, o/m/p-nitro benzaldehyde, m/p-hydroxy benzaldehyde, N,N, dimethyl benzaldehyde, 3,4,5 tri methoxy benzaldehyde to produce corresponding substituted tetraphenyl porphyrins.

Zeolites used in the present invention are commercially available, and can also be prepared by methods known in the art. The zeolite used in the present invention may be any of an alkali ion form such as sodium, potassium or the like, ammonium ion form and proton form. The alkali ion, however, is not preferably because it lowers the catalytic activity if it remains in the catalyst finally. The microwave power varied from low to high power and the time of heating also varied from 3 minutes to 25 minutes. The catalyst weight can be varied in this reaction from 0.1 g to 1 g and the pyrrole to aldehyde molar ratio can be varied from 1:1 to 1:4.

In the reaction an equimolar ratio of pyrrole and benzaldehyde were dissolved in a suitable solvent (chloroform/dichloromethane) for thorough mixing and then the sovent was evaporated. To this, the pre-calcined and dried (200° C., 3 h) MCM-41 catalyst was added to and after mixing thoroughly with a glass rod, is subjected to microwave irradiation for 15 minutes with 2 minutes intervals. Then after the reaction, (20×5) ml chloroform solvent was added to extract the organic compound and then the catalyst is subjected soxhlet extraction with chloroform. Then porphyrin was seperated by columun chromatography over neutral alumina with hexane as eluent (DCM :Hexane). The quantification was alos done by HPLC and compared with the isolate yields and are characterised by Mass and UV-VIS. Along with the cyclized product, tetraphenyl porphyrin, minor amounts of linear chain condensed products of pyrrole and aldehyde were compounds are also formed.

In place of MCM-41 catalyst when HY was used, a small amount of porphyrin is formed, whereas HZSM-5 (30) yields major amount of porphyrin which may be due to surface reaction. The reaction was compared with SAPO-5 and also with silica alumina catalyst and low conversions and selectivities of the porphyrin molecules under microwave irradiation were observed.

The regeneration of the catalyst is easily effected according to any conventional method. For example the carbon deposited on the catalyst can be burned out by passing air through the catalyst layer at a temperature of 450° C. to 550° C.

By using the catalyst of the present invention, as shown, for example, in Example 1, the yield of tetraphenyl porphyrin 23.5%. The yields being shown are as the value calculated based on the conversion of pyrrole. The present invention is described below in more detail referring to Examples, to which the present invention is not limited. By replacing the benzaldehyde with substituted benzaldehydes corresponding tetra substituted porphyrins were formed, which were characterised by UV-VIS spectroscopy.

EXAMPLE 1

Mesoporous molecular sieve MCM-41 was synthesized according to C. T. Kresge et al, Nature 359 (1992) 710, as follows.

Solution A was prepared by mixing 0.38 g of NaOH, 20 ml of water, 0.76 g of Aluminium isoproxide and heated till a clear solution was obtained. After this 9.8 ml of Tetra ethyl ammonium hydroxide was added while cooling the mixture.

Solution B was prepared by mixing 11.6 ml (9.6 g) of 50wt % ludox silica in 50 ml of distilled water the mixture was kept under vigorous stirring until a clear solution formed.

Solution A was added to Solution B under vigorous stirring and kept for stirring for one hour, after that 10.55 g of Hexadecyl trimethyl ammonium bromide (HDTMABr). The pH was adjusted to 10.5.

A stainless steel autoclave having 0.6 liters of volume was charged with the above solution. The autoclave was sealed and heated to 100° C. Hydrothermal synthesis was effected under this condition while continuing stirring for 20 hours. In this period, the inner pressure of the autoclave was 5 to 6 $kg/cm^2$.

After completion of the reaction, the reaction mixture was cooled to room temperature and the product was separated by filtration. After repetition of washing and filtration until the concentration of $Br^-$ ion in the filtrate became 1 ppm or below, the product was dried at 110° C. for 16 hours and then calcined in air at 500° C. for 12 hours to elute the surfactant and obtain white crystals of Na form Al-MCM-41. As a result of the measurement of X-ray diffraction, the crystals had a diffraction pattern coincident with that of MCM-41 reported in Nature 1992 by Breck et al.

EXAMPLE 2

In a test tube, 1 ml of pyrrole and corresponding volume of benzaldehyde (1:1 Molar) are dissolved in chloroform solvent and then the solvent was evaporated. To this, pre-calcined and dried 0.5 g MCM-41 catalyst was added, and after thorough mixing with a glass rod, subjected to microwave irradiation at a power of 2450 MHz for 15 minutes with 2 minutes intervals. After the reaction, the catalyst was thoroughly washed (20×5 ml) with solvent and subjected to soxhlet extraction with chloroform. Porphyrin was separated by column chromatography using neutral alumina and hexane as eluent. The quantification was also done by HPLC and confirmed by isolated yields. Further the products were further confirmed by Uv-Visible spectroscopy and Mass spectroscopy. Average yields of the products found 23.5% of tetraphenyl porphyrin when pyrrole reacted with benzaldehyde over Al-MCM-41.

EXAMPLE 3

The reaction carried out in same manner as in Example 2 with HY catalyst. The yield of tetraphenyl porphyrin is 5%.

EXAMPLE 4

The reaction carried out in same manner as in Example 2 with HZSM-5 (30) catalyst. The yield is 28.0%.

EXAMPLE 5

The reaction was carried in same manner as in Example 2 except ortho hydroxy benzaldehyde was used instead of benzaldehyde with good yield.

EXAMPLE 6

The reaction was carried in same manner as in Example 2 except para methoxy benzaldehyde was used instead of benzaldehyde with good yield.

EXAMPLE 7

The reaction was carried in same manner as in Example 2 except N,N dimethyl benzaldehyde was used instead of benzaldehyde with good yield.

EXAMPLE 8

The reaction was carried in same manner as in Example 2, except para methyl benzaldehyde was used instead of benzaldehyde with good yield.

EXAMPLE 9

The reaction was carried in same manner as in Example 2, except 3,4,5 trimethoxyl benzaldehyde was used instead of benzaldehyde with good yield.

ADVANTAGES OF THE INVENTION

The present invention provides an improved process that comprises environmentally clean technology with low wastage, easy separable and reusability of the catalyst.

The catalysts used in this process are easily separable by the simple filtration.

This process provides an eco-friendly method with higher selectivity.

A method provides a selective heterogeneous catalyst with longer life.

We claim:

1. A process for synthesizing a tetraphenyl porphyrin compound comprising reacting a pyrrole with an aromatic aldehyde in the presence of a zeolite molecular sieve catatyst under microwave radiation at a frequency effective to obtain the tetraphenyl porphyrin compound.

2. A process as claimed in claim 1 wherein the zeolite molecular sieve catalyst is in alkali ion form, ammonium ion form or proton form.

3. A process as claimed in claim 2, where the zeolite molecular sieve catalyst is in alkali ion form and comprises an alkali ion selected from the group consisting of sodium and potassium.

4. A process as claimed in claim 1, wherein the zeolite molecular sieve catalyst is selected from the group consisting of MCM-41, Al-MCM-41, HY, SAPO-5 ZSM 5 and HZSM-5.

5. A process as claimed in claim 1, wherein the aromatic aldehyde is of the formula RPhCHO, wherein R in the ortho, meta and para positions is selected from the group consisting of methoxy, N, N, dimethyl, hydroxy and nitro.

6. A process as claimed in claim 1, wherein the aromatic aldehyde is selected from the group consisting of benzaldehyde, o/m/p-methoxy benzaldehyde, o/m/p-methyl benzaldehyde, o/m/p-nitro benzaldehyde, m/p-hydroxy benzaldehyde, N, N, dimethyl benzaldehyde and 3,4,5 tri methoxy benzaldehyde.

7. A process as claimed in claim 1, wherein the pyrrole and the aldehyde are reacted at a pyrrole to aldehyde molar ratio in the range of 1:1 to 1:4.

8. A process as claimed in claim 1, wherein the catalyst is regenerated by burning out carbon deposited thereon by passing air through a layer of the catalyst at a temperature in the range of 450° C. to 550° C.

9. A process as claimed in claim 1, wherein the time period for the microwave radiation is in the range of 3 minutes to 30 minutes.

10. A process as claimed in claim 1, wherein the process is conducted so as to yield at least 23.5% of the tetraphenyl porphyrin compound, said compound having the formula 1:

Formula 1

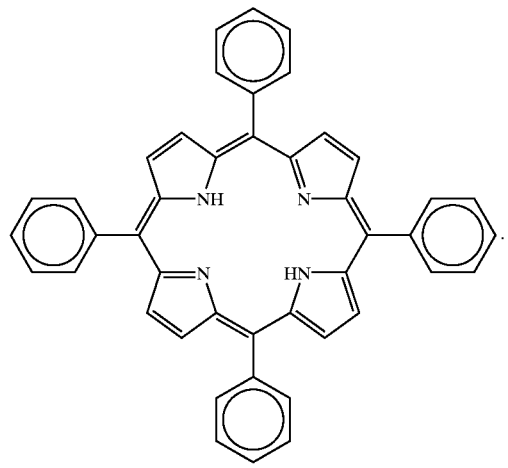

* * * * *